(12) United States Patent
Camisa et al.

(10) Patent No.: US 12,232,742 B2
(45) Date of Patent: Feb. 25, 2025

(54) SYSTEMS AND METHODS FOR ENDOSCOPIC SUBMUCOSAL DISSECTION

(71) Applicant: Covidien LP, Mansfield, MA (US)

(72) Inventors: William Camisa, Los Altos, CA (US); Damian Muldoon, County Galway (IE); Damian Carr, Galway (IE); Rory O'Brien, County Tipperary (IE); Shane Ward, Galway (IE)

(73) Assignee: Covidien LP, Mansfield, MA (US)

( * ) Notice: Subject to any disclaimer, the term of this patent is extended or adjusted under 35 U.S.C. 154(b) by 566 days.

(21) Appl. No.: 17/610,820

(22) PCT Filed: May 1, 2020

(86) PCT No.: PCT/US2020/030907
§ 371 (c)(1),
(2) Date: Nov. 12, 2021

(87) PCT Pub. No.: WO2020/231646
PCT Pub. Date: Nov. 19, 2020

(65) Prior Publication Data
US 2022/0211385 A1    Jul. 7, 2022

Related U.S. Application Data

(60) Provisional application No. 62/848,668, filed on May 16, 2019.

(51) Int. Cl.
*A61B 17/00*    (2006.01)
*A61B 17/122*    (2006.01)
(Continued)

(52) U.S. Cl.
CPC ........ *A61B 17/1285* (2013.01); *A61B 17/122* (2013.01); *A61B 2017/00358* (2013.01)

(58) Field of Classification Search
CPC ..... A61B 17/08; A61B 17/083; A61B 17/122; A61B 17/1285; A61B 17/128; A61B 2017/00358; A61B 2017/081
See application file for complete search history.

(56) References Cited

U.S. PATENT DOCUMENTS

2008/0294178 A1* 11/2008 Kortenbach ....... A61B 1/00087
606/142
2017/0215886 A1* 8/2017 Muyari ................ A61B 17/122
2018/0140300 A1   5/2018 Randhawa

FOREIGN PATENT DOCUMENTS

CN    103315792 A    9/2013
CN    208355513 U    1/2019
(Continued)

OTHER PUBLICATIONS

International Search Report and Written Opinion dated Aug. 28, 2020, issued in corresponding International Appln. No. PCT/US2020/030907, 16 pages.
(Continued)

*Primary Examiner* — Kelly J Bekker
*Assistant Examiner* — Lindsey R. Rivers
(74) *Attorney, Agent, or Firm* — Carter, DeLuca & Farrell LLP

(57) ABSTRACT

A surgical clip includes an elongated body configured to be detachably coupled to a shaft of a surgical instrument, a pair of jaw members received in the body, and a release feature for selectively unlocking the jaw members.

16 Claims, 5 Drawing Sheets

(51) Int. Cl.
*A61B 17/128* (2006.01)
*A61B 17/29* (2006.01)
*A61B 17/3205* (2006.01)

(56) References Cited

FOREIGN PATENT DOCUMENTS

| | | | |
|---|---|---|---|
| JP | 2003513737 A | 4/2003 | |
| JP | 2013085859 A | 5/2013 | |
| JP | 5750619 B2 | 7/2015 | |
| JP | 2015192724 A | 11/2015 | |
| JP | 2015192725 A | 11/2015 | |
| WO | WO-2009155286 A1 * | 12/2009 | ....... A61B 17/00234 |
| WO | 2018235402 A1 | 12/2018 | |
| WO | WO-2018227592 A1 * | 12/2018 | ........... A61B 17/122 |

OTHER PUBLICATIONS

Interational Preliminary Report on Patentability dated Nov. 16, 2021, issued in corresponding International Appln. No. PCT/US2020/030907, 8 pages.

Notice of Allowance issued in corresponding Japanese Application No. 2021-568273 dated Apr. 26, 2024, English language translation not available. (3 pages).

Office Action issued in corresponding Chinese Application No. 2020800362453 dated Jun. 6, 2024, together with English language translation retrieved from the Global dossier (13 pages).

* cited by examiner

SYSTEMS AND METHODS FOR ENDOSCOPIC SUBMUCOSAL DISSECTION

CROSS-REFERENCE TO RELATED APPLICATION

This application claims benefit of and priority to U.S. Provisional Application No. 62/848,668, filed May 16, 2019, which is incorporated herein by reference in its entireties.

FIELD

The present technology is related generally to surgical clips used in endoscopic submucosal dissection.

BACKGROUND

Endoscopic resection has been accepted as a first choice for the treatment of early stage GI carcinomas because of reduced invasiveness and lower cost relative to other treatment options. Endoscopic submucosal resection (ESD) allows for an en bloc resection and accurate histopathological diagnosis regardless of the size, an existence of severe fibrosis at the submucosal layer, and the location of a lesion. One of the benefits of ESD is lower recurrence rates compared to endoscopic mucosal resection. During some ESD procedures, jaw members of a surgical clip are engaged to tissue. After performing the dissection, the jaw members are disengaged from the tissue.

SUMMARY

In one aspect, the present disclosure provides a surgical clip including an inner body, first and second jaw members coupled to the inner body, and a release lever. The first and second jaw members are configured to move between an open configuration and a closed configuration to grasp tissue therebetween. The release lever is movably coupled to the inner body and disposed adjacent a proximal end portion of the first jaw member. The release lever is engagable with the proximal end portion of the first jaw member to move a distal end portion of the first jaw member away from a distal end portion of the second jaw member.

In aspects, the release lever may include a proximal end portion accessible via a slot defined in the inner body.

In aspects, the release lever may have a distal end portion pivotably coupled to the inner body, and the proximal end portion of the release lever may be configured to pivot about the distal end portion thereof.

In aspects, the surgical clip may further include an outer body disposed about the inner body. The outer body may have a portion that defines a slot that overlaps the slot of the inner body. At least the portion of the outer body may have an oval transverse cross-sectional shape.

In aspects, the release lever may have a T-shaped configuration, and the inner body may define a T-shaped slot in which the release lever is received.

In aspects, the proximal end portion of the first jaw member is movably received in a longitudinally-extending channel defined in the inner body In aspects, the channel may have an enlarged proximal end portion in which the proximal end portion of the first jaw member is received when the first and second jaw members are in the closed configuration.

In aspects, the release lever may have a tab received in the proximal end portion of the channel.

In aspects, the channel may have a distal end portion. The distal end portion of the first jaw member may move toward the distal end portion of the second jaw members as the proximal end portion of the first jaw member moves proximally through the distal end portion of the channel.

In aspects, the first and second jaw members may be configured to move through the channel between a proximal position, in which the first and second jaw members are selectively fixed in the closed configuration, and a distal position, in which the first and second jaw members are in the open configuration.

In aspects, the proximal end portion of the first jaw member may extend laterally from the first jaw member and be at least partially received in the channel.

In aspects, the surgical clip may further include a pivot member axially restrained with the first and second jaw members and axially slidable within the inner body, such that retraction of the pivot member approximates the first and second jaw members and advancement of the pivot member moves the first and second jaw members away from each other.

In aspects, the second jaw member may remain in a fixed position relative to the inner body when the release lever is actuated.

In accordance with another aspect of the disclosure, a surgical system for performing an endoscopic submucosal dissection is provided. The system includes a snare and a surgical clip. The surgical clip includes an inner body, first and second jaw members, and a release lever. The inner body defines a slot, and the first and second jaw members are at least partially received in the inner body. The first and second jaw members are configured to move between an open configuration and a closed configuration to grasp tissue therebetween. The release lever is movably coupled to the inner body and configured to be actuated by the snare via the slot in the inner body. The first jaw member has a distal end portion configured to move away from a distal end portion of the second jaw member in response to the snare actuating the release lever.

In aspects, the first jaw member may include a proximal end portion movably received within a channel defined in the inner body.

In aspects, the channel may have an enlarged proximal end portion in which the proximal end portion of the first jaw member is received when the first and second jaw members are in the closed configuration.

In aspects, the first and second jaw members may be configured to move through the channel between a proximal position, in which the first and second jaw members are releasably fixed in the closed configuration, and a distal position, in which the first and second jaw members are in the open configuration.

In aspects, the proximal end portion of the first jaw member may extend laterally from the first jaw member and be at least partially received in the channel.

In aspects, the second jaw member may remain in a fixed position relative to the inner body when the release lever is actuated by the snare.

In accordance with yet another aspect of the disclosure, a method of performing an endoscopic submucosal dissection is provided. The method includes deploying a surgical clip, approximating a pair of jaws of the surgical clip about tissue, and actuating a release lever of the surgical clip, whereby the release lever pivots the first jaw member away from the second jaw member to release the tissue from the first and second jaw members.

BRIEF DESCRIPTION OF THE DRAWINGS

Objects and features of the presently disclosed surgical clips will become apparent to those of ordinary skill in the art when descriptions of various embodiments thereof are read with reference to the accompanying drawings, of which.

DETAILED DESCRIPTION

The disclosure is generally directed to surgical clips including a tubular body, a pair of jaw members received in and deployable from the tubular body, and a release feature for selectively unlocking one of the jaw members. When the jaw members are closed about tissue and in a locked state, the jaw members may be released from the locked state by activating the release feature. These and other aspects of the present disclosure are described in greater detail below.

Figure 1:
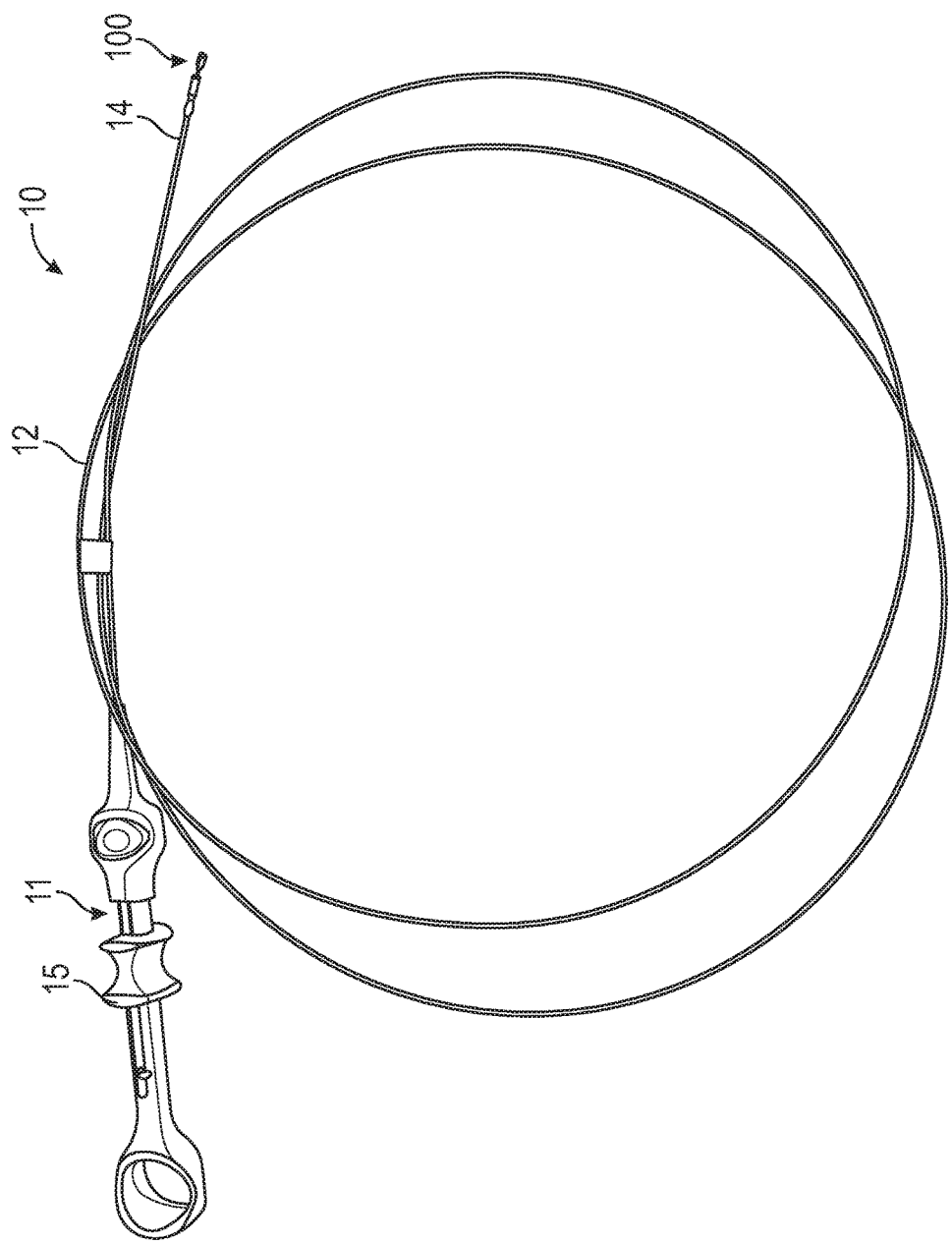
FIG. 1 is a perspective view illustrating an exemplary embodiment of a hand-held surgical instrument including a handle assembly, a flexible shaft, and a surgical clip coupled to a distal end portion of the flexible shaft.

FIG. 1 illustrates a hand-held surgical instrument 10 for deploying a surgical clip 100. The surgical instrument 10 generally includes a handle assembly or actuator 11, a shaft 12 extending distally from the handle assembly 11, and a surgical clip 100 detachably coupled to a distal end portion 14 of the shaft 12. In some aspects, instead of the clip 100 being deployable from a hand-held instrument, the clip 100 may be deployed from a surgical robotic arm.

The surgical instrument 10 includes an actuation mechanism, such as, for example, a puller (not shown) axially movable within the shaft 12. The puller may have a proximal end operably coupled to a trigger 15 of the handle assembly 11, such that an actuation of the trigger 15 proximally translates the puller. The puller may have a distal end detachably coupled to the surgical clip 100, such that proximal translation of the puller moves the surgical clip 100 from an open configuration to a closed configuration, as will be described. It is contemplated that the surgical instrument 10 may include any suitable actuation mechanism for deploying the surgical clip 100, such as a drive rod or a drive tube.

Figure 2:
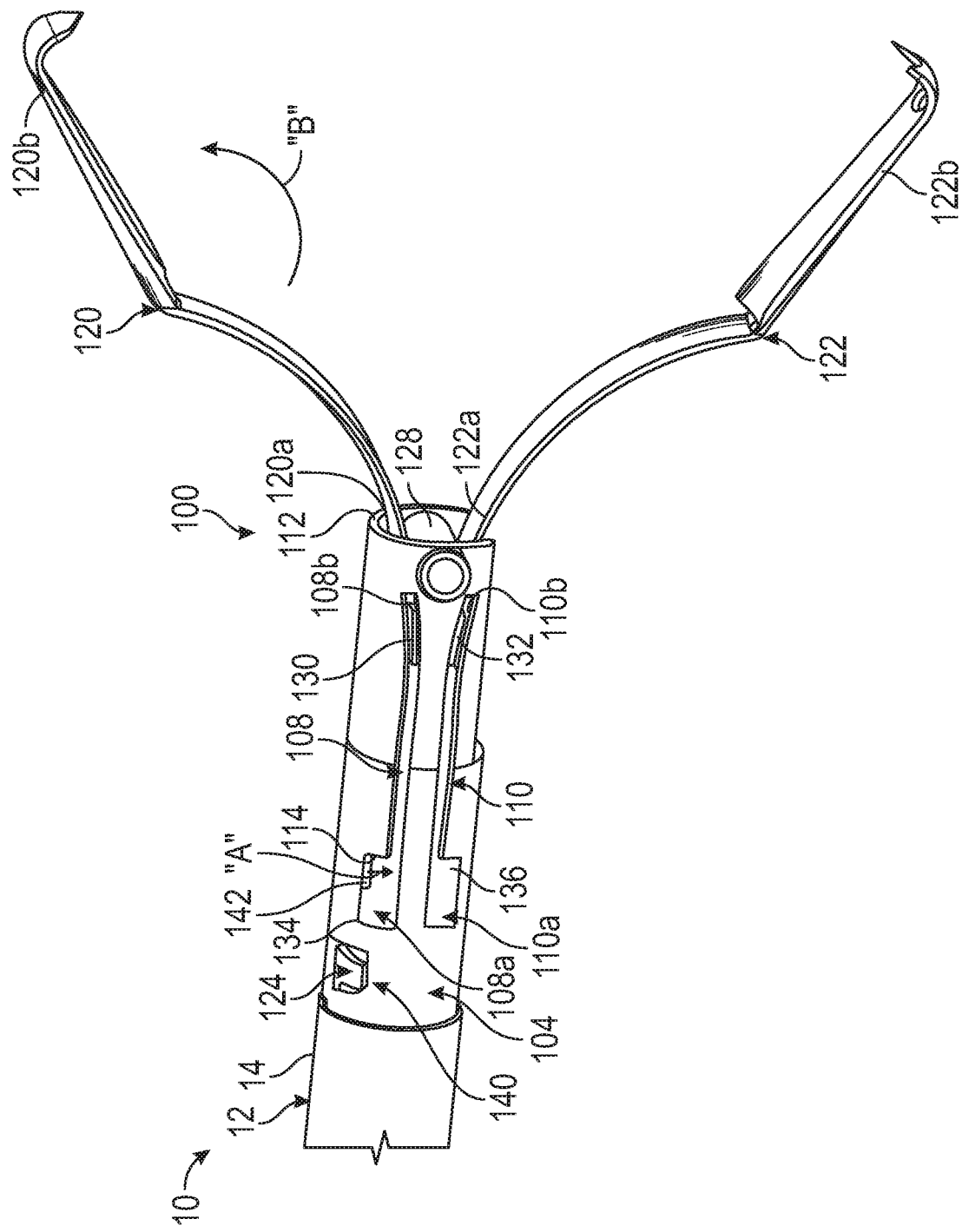
FIG. 2 is a side, perspective view illustrating the surgical clip of FIG. 1, with an outer body removed.
Figure 3A:
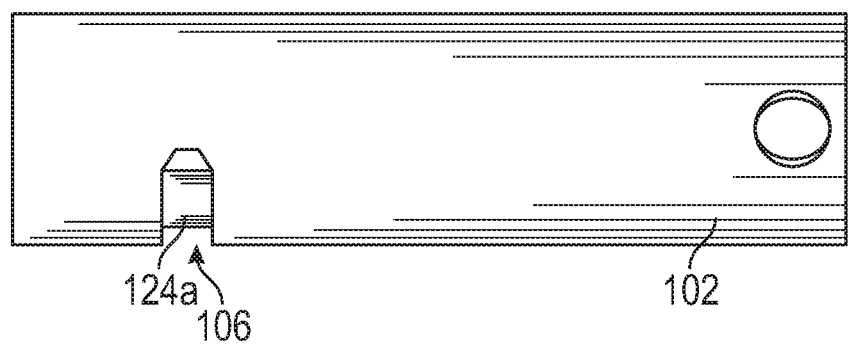
FIG. 3A is a side view of an outer body and a release lever of the surgical clip of FIG. 1.
Figure 3B:
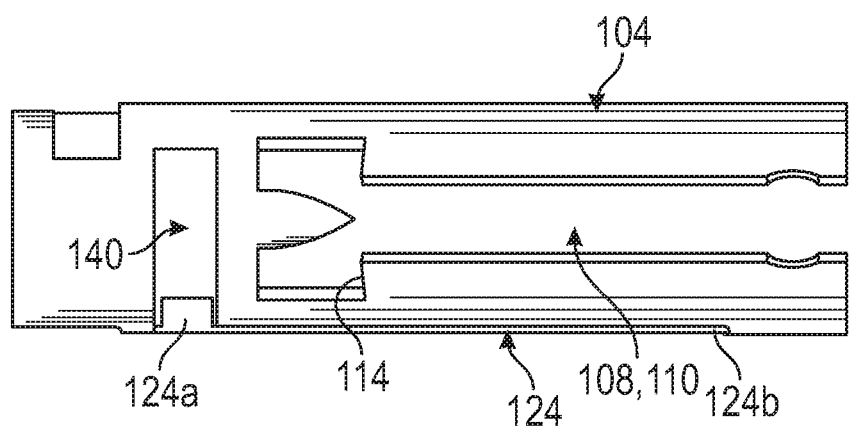
FIG. 3B is a side view of an inner body and the release lever of the surgical clip of FIG. 1.
Figure 3C:
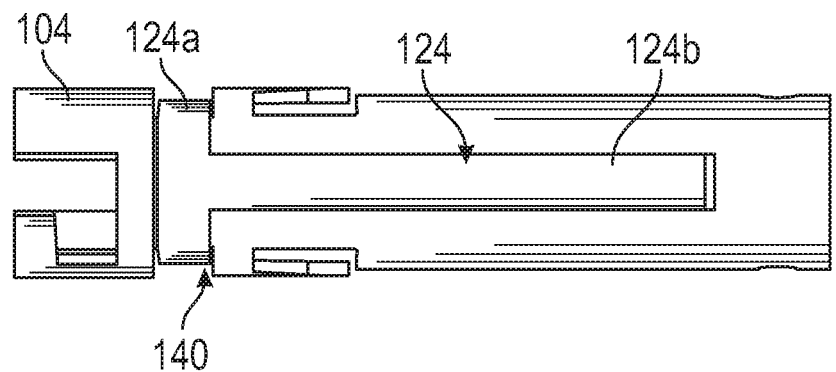
FIG. 3C is a top view of the inner body and release lever of the surgical clip of FIG. 1.

With reference to FIGS. 2-3C, the surgical clip 100 has a tubular outer body 102 and a tubular inner body 104 received in the outer body 102. The outer body 102 is configured to be detachably coupled to the distal end 14 of the shaft 12. In aspects, the shaft 12 may have a release latch (not shown) coupled to the outer body 102 and an actuation mechanism (e.g., a pull rod, not shown) for actuating the release latch to deploy the surgical clip 100 from the shaft 12. The outer body 102 has a hollow interior and defines a slot 106 (FIG. 3A) providing access into the hollow interior. The inner body 104 defines first and second longitudinally-extending channels 108, 110 in a tubular wall 112 thereof. In some embodiments, the first and second channels 108, 110 may be joined, thereby forming one continuous channel, as shown in FIG. 3B. The channels 108, 110 may cooperatively define a T-shaped configuration, wherein each of the channels 108, 110 has an enlarged proximal end portion 108a, 110a, and a distal end portion 108b, 110b. The tubular wall 112 of the inner body 104 has a stop surface 114 configured to resist advancement of a proximal end portion 120a of a first jaw member 120 when the proximal end portion 120a of the first jaw member 120 is received in the proximal end portion 108a of the first channel 108, as will be described further below. In a distal direction, the distal end portion 108b, 110b of each of the channels 108, 110 may extend away from a central longitudinal axis of the inner body 104, as shown in FIG. 2.

The surgical clip 100 includes first and second jaw members 120, 122 coupled to the inner body 104. Each of the first and second jaw members 120, 122 has a proximal end portion 120a, 122a slidably received in the hollow interior of the inner body 104, and a distal end portion 120b, 122b disposed distally of the inner body 102. The distal end portion 120, 122b of the jaw members 120, 122 may define teeth (not shown) for assisting in grasping tissue between the jaw members 120, 122. The jaw members 120, 122 are resiliently biased toward an open configuration due to the shape and structure of the individual jaw members 120, 122. For example, each of the jaw members 120, 122 may be curved outwardly away from one another. In some aspects, the jaw members 120, 122 may be resiliently biased toward the open configuration by a biasing member (not shown). Alternately, the jaw members 120, 122 may be devoid of a resilient bias.

The jaw members 120, 122 are axially movable relative to the inner body 104 from a proximal position, in which the distal end portion 120b, 122b of the jaw member 120, 122 are approximated, and a distal position, in which the distal end portion 120b, 122b of the jaw members 120, 122 are spaced from one another. The proximal end portions 120a, 122a of the respective jaw members 120, 122 remain separated by a pivot member 128 disposed therebetween. The pivot member 128 is axially restrained with the proximal end portion 120a, 122a of the jaw members 120, 122 and axially slidable within the inner body 104, such that the jaw members 120, 122 retract and advance with the pivot member 128. The pivot member 128 may be detachably coupled to the distal end portion of the puller and axially movable relative to the inner body 104 by the puller.

The proximal end portions 120a, 122a of the respective first and second jaw members 120, 122 has a tab or appendage 130, 132 extending laterally therefrom. The tab 130, 132 of each of the first and second jaw members 120, 122 is received in a respective channel 108, 110 of the inner body 104. As the proximal end portion 120a, 122a of each of the jaw members 120, 122 is translated within the inner body 104, the tabs 130, 132 move through the respective channels 108, 110 between a proximal position, in which the tabs 130, 132 are received in the enlarged section 134, 136 of the proximal end portions 108a, 110a of the channels 108, 110, and a distal position, in which the tabs 130, 132 are received in the ramped distal end portions 108b, 110b of the channels 108, 110.

Coupled to the inner body 104 of the surgical clip 100 is a release lever 124, which assumes a T-shaped configuration and is received in a T-shaped slot 140 defined in the tubular wall 112 of the inner body 104. In some aspects, the release lever 124 may assume any suitable shape, such as linear. The release lever 124 has a proximal end portion 124a accessible through the slots 106, 140 of the outer body 102 and inner body 104, respectively, and a distal end portion 124b pivotably coupled (e.g., via a hinge) to the tubular wall 112 of the inner body 104. The proximal end portion 124a of the release lever 124 is pivotable about the distal end portion 124b thereof upon receiving a threshold force. The release lever 124 has a tab or appendage 142 (FIG. 2) extending laterally therefrom that is received in the enlarged section 134 of the proximal end portion 108a of the first channel 108. The tab 142 is configured to move out of the enlarged section 134 of the channel 108 toward a central longitudinal axis of the first channel 108 in response to an actuation of the release lever 124.

Figure 4:
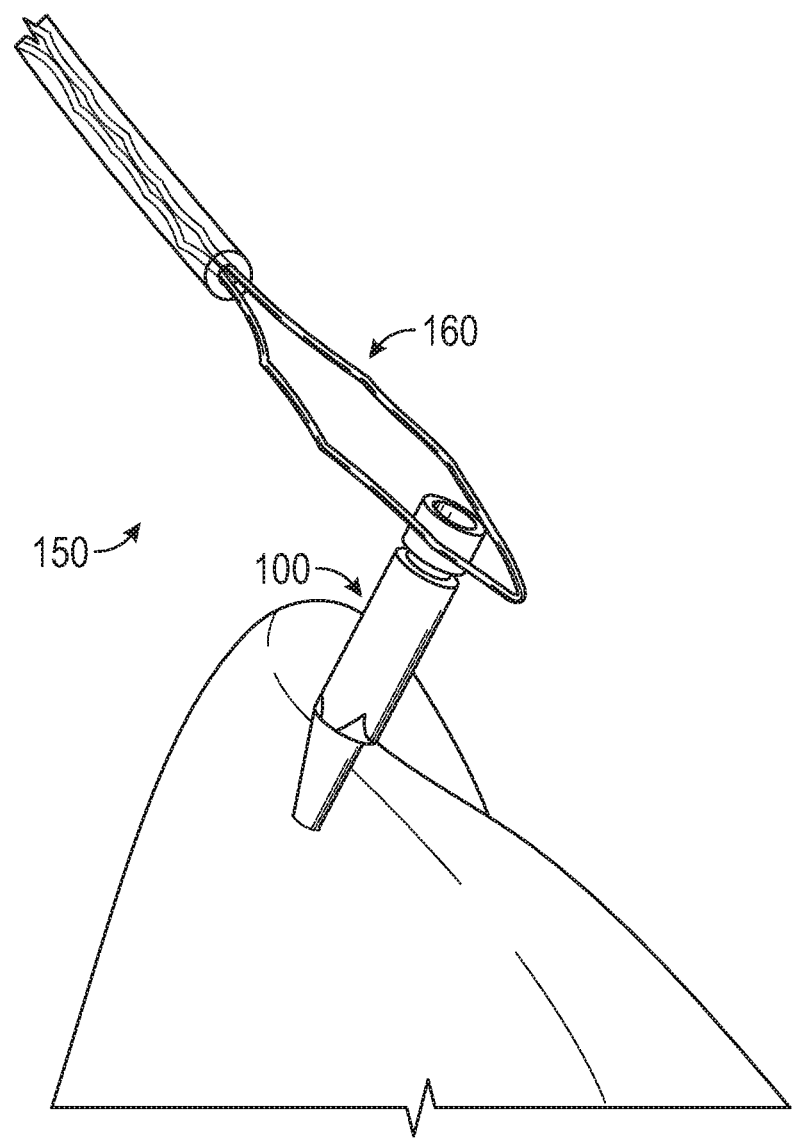
FIG. 4 is a perspective view illustrating a surgical system including the surgical clip of FIG. 1 and a snare for releasing the surgical clip from tissue.

FIG. 4 illustrates a surgical system 150 including the surgical clip 100 and a snare 160. The snare 160 is configured to actuate the release lever 124 of the surgical clip 100 to release the jaw members 120, 122 of the surgical clip 100 from tissue. In aspects, the surgical system 150 may include any other suitable surgical device for actuating the release lever 124.

In use, with the surgical clip 100 coupled to the shaft 12 and the jaw members 120, 122 in the open configuration, the surgical clip 100 is positioned adjacent tissue. The tissue is positioned between the jaw members 120, 122, whereupon the trigger 15 is retracted to retract the puller and, in turn, the pivot member 128. As the pivot member 128 retracts, the proximal end portions 120a, 122a of the respective jaw members 120, 122 are moved proximally through the inner body 104, whereby the tubular wall 112 of the inner body 104 acts on the jaw members 120, 122 to move the jaw members 120, 122 toward the closed configuration. Further, the jaw members 120, 122 are also caused to approximate as the tabs 130, 132 of the respective first and second jaw members 120, 122 move proximally out of the distal end portions 108b, 110b of the respective channels 108, 110. Upon the tabs 130, 132 of the jaw members 120, 122 entering the proximal end portions 108a, 110a of the channels 108, 110, the tabs 130, 132 flex outwardly into the enlarged section 134 of the proximal end portions 108a, 110a of the channels 108, 110, thereby locking the jaw members 120, 122 in the closed configuration about the lesion.

With the tissue grasped between the jaw members 120, 122, the puller is further retracted to detach the puller from the jaw members 120, 122, thereby releasing the outer body 102 of the surgical clip 100 from the shaft 12 and leaving the surgical clip 100 at the desired location. Other mechanisms for releasing the surgical clip 100 from the shaft 12 are also contemplated.

When removal of the surgical clip 100 is desired, the snare 160, or any other suitable grasping device (e.g., a forceps), may be positioned in the slot 106 of the outer body 102. The snare 160 is cinched to pass the snare 160 through the slot 106 of the outer body 102, into the slot 140 of the inner body 104, and into engagement with the proximal end portion 124a of the release lever 124. Further cinching of the snare 160 pivots the proximal end portion 124a of the release lever 124 relative to the inner body 104 to move the tab 142 of the release lever 124 in the direction indicated by arrow "A" in FIG. 2. The tab 142 of the release lever 124 drives the tab 130 of the first jaw member 120 off of the stop surface 114 of the inner body 104 and out of the enlarged section 134 of the proximal end portion 108a of the first channel 108. Movement of the tab 130 of the first jaw member 120 out of the enlarged section 134 causes the distal end portion 120b of the first jaw member 120 to pivot, in the direction indicated by arrow "B" in FIG. 2, away from the distal end portion 122b of the second jaw member 122, thereby releasing the tissue from between the jaw members 120, 122.

Since the tab 142 of the release lever 124 is only engaged with the first jaw member 120, actuating the release lever 124 only moves the first jaw member 120 while the second jaw member 122 remains in a fixed position relative to the inner body 104. Since only one of the jaw members 120, 122 is released, removal of the surgical clip 100 from tissue is simplified. Further, the elongated configuration of the release lever 124 improves its responsiveness and serves to minimize the force required to actuate the release lever 124.

Figure 5:
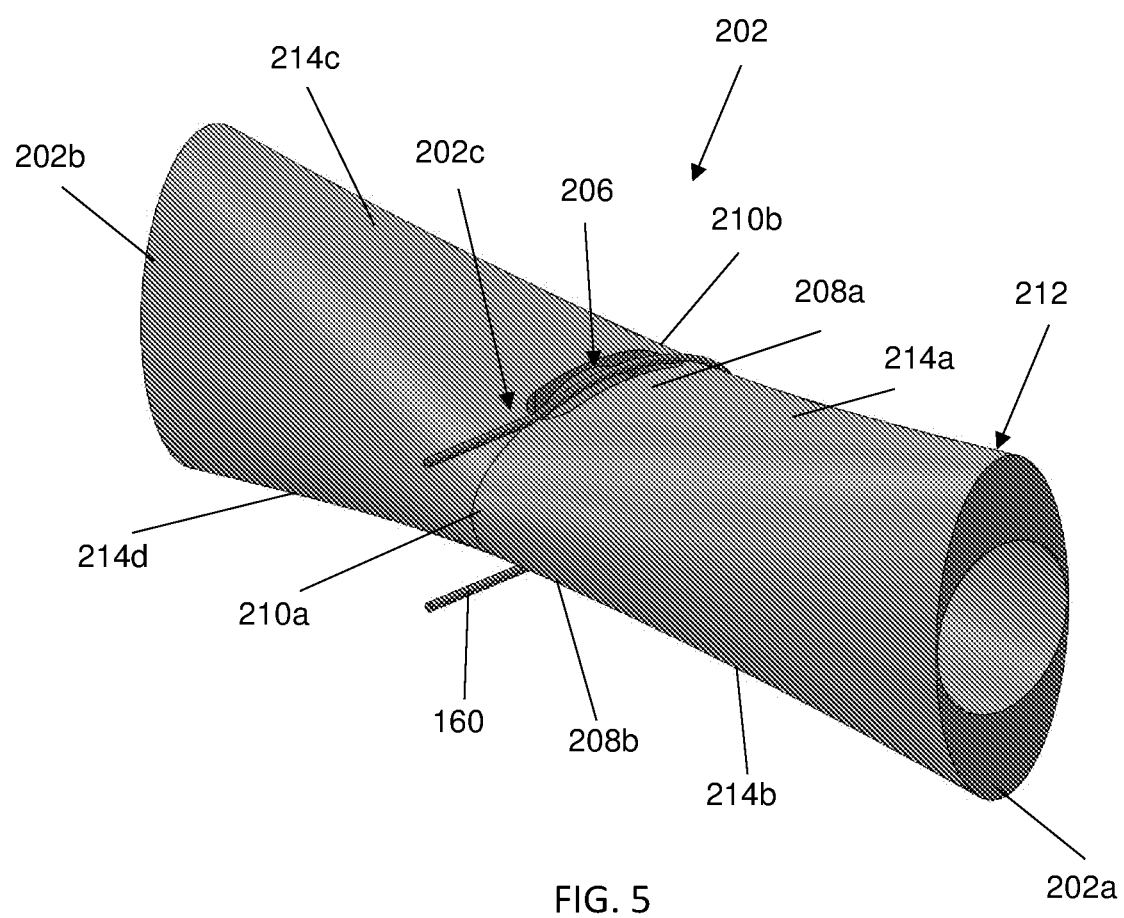
FIG. 5 is a perspective view illustrating another aspect of an outer body of the surgical clip of FIG. 1.

With reference to FIG. 5, an alternate aspect of an outer body 202 for use with the inner body 102 (FIG. 2) of the surgical clip 100 is illustrated. The outer body 202 is similar to the outer body 102 of FIG. 3A except the outer body 202 has an elliptical or oval transverse cross-sectional shape configured to rotationally align a slot 206 of the outer body 202 with a snare, such as, for example, snare 160.

More specifically, the outer body 202 has first and second ends 202a, 202b and a middle portion 202c, which defines the slot 206 therein. The middle portion 202c has a pair of opposed wide sides 208a, 208b, one of which defining the slot 206 therein, and a pair of opposed narrow sides 210a, 210b. The outer body 202 has an outer surface 212 that tapers from the first end 202a toward each of the wide sides 208a, 208b of the middle portion 202c to define opposed first and second ramped surfaces 214a, 214b. The outer surface 212 also tapers from the second end 202b toward each of the wide sides 208a, 208b of the middle portion 202c to define opposed third and fourth ramped surfaces 214c, 214d. The ramped surfaces 214a, 214b, 214c, 214d assist a clinician by guiding the snare toward the slot 206 in the middle portion 202c. It is contemplated that the outer body 202 may be formed by compressing a middle portion of an oval-shaped hypotube. In aspects, the inner body 102 (FIG. 2) may have an oval-shaped transverse cross-section.

In use, a clinician may attempt to position a snare 160 into the slot 206 of the outer body 202 to engage the release lever 124 (FIG. 3A). In instances where the snare 160 is improperly positioned relative to the slot 206, such as on the narrow sides 210a, 210b of the middle portion 202c, and therefore out of alignment with the slot 206, the outer body 202 along with the remainder of the surgical clip 100 may be caused to rotate up to 90 degrees about the longitudinal axis of the outer body 202 to align the long portion of the snare 160 with the slot 206.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques).

What is claimed is:
1. A surgical clip, comprising:
an inner body having a slot defined in the inner body and an outer surface and first and second longitudinally-extending channels defined through the outer surface; an outer body disposed about the inner body, the outer body having a portion defining a slot that overlaps the slot defined in the inner body; first and second jaw members coupled to the inner body and configured to move between an open configuration and a closed configuration to grasp tissue therebetween, each of the first and second jaw members having a tab extending laterally from a proximal end portion of the respective first and second jaw members, wherein during movement of the first and second jaw members between the open and closed configurations, the tab of the first jaw member moves within the first longitudinally-extending channel and the tab of the second jaw member moves within the second longitudinally-extending channel; and a release lever movably coupled to the inner body and disposed adjacent the proximal end portion of the first jaw member, wherein the release lever is engageable with the proximal end portion of the first jaw member to move a distal end portion of the first jaw member away from a distal end portion of the second jaw member.

2. The surgical clip according to claim 1, wherein the release lever includes a proximal end portion accessible via the slot defined in the inner body.

3. The surgical clip according to claim 2, wherein the release lever has a distal end portion pivotably coupled to the inner body, the proximal end portion of the release lever configured to pivot about the distal end portion thereof.

4. The surgical clip according to claim 1, wherein at least the portion of the outer body has an oval transverse cross-sectional shape.

5. The surgical clip according to claim 1, wherein the release lever has a T-shaped configuration, and the inner body defines a T-shaped slot in which the release lever is received.

6. The surgical clip according to claim 1, wherein each of the first and second longitudinally-extending channels has an enlarged proximal end portion in which the respective tabs of the first and second jaw members is received when the first and second jaw members are in the closed configuration.

7. The surgical clip according to claim 6, wherein the release lever has a tab received in the proximal end portion of the first longitudinally-extending channel.

8. The surgical clip according to claim 1, wherein the distal end portion of the first jaw member moves toward the distal end portion of the second jaw member as the tabs of the respective first and second jaw members move proximally through a distal end portion of the respective first and second longitudinally-extending channels.

9. The surgical clip according to claim 1, wherein the tabs of the respective first and second jaw members are configured to move through the respective first and second longitudinally-extending channels between a proximal position, in which the first and second jaw members are selectively fixed in the closed configuration, and a distal position, in which the first and second jaw members are in the open configuration.

10. The surgical clip according to claim 1, further comprising a pivot member axially restrained with the first and second jaw members and axially slidable within the inner body, such that retraction of the pivot member approximates the first and second jaw members and advancement of the pivot member moves the first and second jaw members away from each other.

11. The surgical clip according to claim 1, wherein the second jaw member remains in a fixed position relative to the inner body when the release lever is actuated.

12. A surgical system for performing an endoscopic submucosal dissection, comprising:
a snare; and
surgical clip including:
    an inner body defining a slot and having first and second longitudinally-extending channels defined through an outer surface of the inner body;
    first and second jaw members at least partially received in the inner body and configured to move between an open configuration and a closed configuration to grasp tissue therebetween, each of the first and second jaw members having a tab extending laterally from a proximal end portion of the respective first and second jaw members, wherein during movement of the first and second jaw members between the open and closed configurations, the tab of the first jaw member moves within the first longitudinally-extending channel and the tab of the second jaw member moves within the second longitudinally-extending channel; and
    a release lever movably coupled to the inner body and configured to be actuated by the snare via the slot in the inner body, wherein the first jaw member has a distal end portion configured to move away from a distal end portion of the second jaw member in response to the snare actuating the release lever.

13. The surgical system according to claim 12, wherein each of the first and second longitudinally-extending channels has an enlarged proximal end portion in which the respective tabs of the first and second jaw members are received when the first and second jaw members are in the closed configuration.

14. The surgical system according to claim 12, wherein the tabs of the respective first and second jaw members are configured to move through the respective first and second longitudinally-extending channels between a proximal position, in which the first and second jaw members are selectively fixed in the closed configuration, and a distal position, in which the first and second jaw members are in the open configuration.

15. The surgical system according to claim 12, wherein the second jaw member remains in a fixed position relative to the inner body when the release lever is actuated by the snare.

16. A method of performing an endoscopic submucosal dissection, comprising:
deploying a surgical clip including a tubular inner body having a slot defined in the inner body and an outer surface and first and second longitudinally-extending channels defined through the outer surface and an outer body disposed about the inner body, the outer body having a portion defining a slot that overlaps the slot defined in the inner body;
approximating a first jaw member and a second jaw member about tissue such that a tab extending laterally from each of the jaw members moves through a respective one of the first and second longitudinally-extending channels; and
actuating a release lever of the surgical clip, whereby the release lever pivots the first jaw member away from the second jaw member to release the tissue from the first and second jaw members.

* * * * *